US010429363B2

United States Patent
Uchiho et al.

(10) Patent No.: US 10,429,363 B2
(45) Date of Patent: Oct. 1, 2019

(54) FAR-ULTRAVIOLET ABSORBANCE DETECTION DEVICE FOR LIQUID CHROMATOGRAPHY

(71) Applicant: Hitachi High-Technologies Corporation, Minato-ku, Tokyo (JP)

(72) Inventors: Yuichi Uchiho, Tokyo (JP); Masao Kamahori, Tokyo (JP); Toshimichi Aota, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 10 days.

(21) Appl. No.: 15/015,386

(22) Filed: Feb. 4, 2016

(65) Prior Publication Data
US 2016/0258913 A1    Sep. 8, 2016

(30) Foreign Application Priority Data

Mar. 3, 2015    (JP) ................................ 2015-041593

(51) Int. Cl.
*G01N 30/74*    (2006.01)
*G01N 30/86*    (2006.01)

(52) U.S. Cl.
CPC ......... *G01N 30/74* (2013.01); *G01N 30/8641* (2013.01)

(58) Field of Classification Search
CPC ..... G01N 30/74; G01N 30/8641; G01J 3/427; G01J 2003/421

(Continued)

(56) References Cited

U.S. PATENT DOCUMENTS 3,986,776 A * 10/1976 George ..................... G01J 3/42
226/146
4,781,456 A * 11/1988 Nogami .................. G01J 3/427
356/320

(Continued)

FOREIGN PATENT DOCUMENTS

JP    63-32351 A    2/1988
JP    4-34341 A    2/1992

(Continued)

OTHER PUBLICATIONS

Noboru Higashi et al., "Direct Determination of Peracetic Acid, Hydrogen Peroxide, and Acetic Acid in Disinfectant Solutions by Far-Ultraviolet Absorption Spectroscopy", Anal. Chem., vol. 77, No. 7, 2005, pp. 2272-2277.

(Continued)

*Primary Examiner* — John Fitzgerald
*Assistant Examiner* — Alexander A Mercado
(74) *Attorney, Agent, or Firm* — Crowell & Moring LLP

(57) ABSTRACT

In order to achieve high sensitivity without an increase in device complexity or cost, a far-ultraviolet absorbance detection device for liquid chromatography is provided with: an optical system including a light source that emits light including far-ultraviolet light, a diffraction grating for dispersing the light emitted from the light source, a flow cell through which a liquid is passed, a slit for selecting a predetermined wavelength of +1 order light diffracted by the diffraction grating and causing the light to enter the flow cell, a first photodetector for detecting the light transmitted by the flow cell, and a second photodetector for detecting light other than the +1 order light diffracted by the diffraction grating; a mechanism for evacuating or substituting the optical system with nitrogen gas; and a computation unit that calculates absorbance from an output signal from the first (Continued)

photodetector and an output signal from the second photodetector. The second photodetector is fixedly disposed.

7 Claims, 8 Drawing Sheets

(58) Field of Classification Search
USPC .......................................................... 73/61.58
See application file for complete search history.

(56) References Cited

U.S. PATENT DOCUMENTS

| | | | | |
|---|---|---|---|---|
| 6,690,469 | B1* | 2/2004 | Shibata | G01N 21/21 |
| | | | | 356/369 |
| 6,916,584 | B2* | 7/2005 | Sreenivasan | B29C 35/0888 |
| | | | | 264/494 |
| 7,027,156 | B2* | 4/2006 | Watts | B29C 35/0888 |
| | | | | 356/400 |
| 7,070,405 | B2* | 7/2006 | Sreenivasan | B29C 35/0888 |
| | | | | 425/174.4 |
| 2007/0279616 | A1 | 12/2007 | Sasayama | |
| 2008/0218734 | A1* | 9/2008 | Higashi | G01N 21/552 |
| | | | | 356/51 |
| 2014/0005128 | A1* | 1/2014 | Mo | A61K 9/1611 |
| | | | | 514/21.5 |
| 2014/0098656 | A1* | 4/2014 | Minami | G11B 7/1353 |
| | | | | 369/112.07 |
| 2014/0132962 | A1* | 5/2014 | Petschik | G01D 5/285 |
| | | | | 356/492 |

FOREIGN PATENT DOCUMENTS

| | | |
|---|---|---|
| JP | 11-108912 A | 4/1999 |
| JP | 2004-12370 A | 1/2004 |
| JP | 2007-322321 A | 12/2007 |

OTHER PUBLICATIONS

Noboru Higashi et al., "An attenuated total reflectance far-UV spectrometer", Review of Scientific Instruments, vol. 78, 103107, 2007 (six (6) pages).

Japanese-language Office Action issued in counterpart Japanese Application No. 2015-041593 dated Oct. 3, 2017 (three (3) pages).

Japanese-language Office Action issued in counterpart Japanese Application No. 2015-041593 dated Apr. 17, 2018 (three (3) pages).

* cited by examiner

US 10,429,363 B2

FAR-ULTRAVIOLET ABSORBANCE DETECTION DEVICE FOR LIQUID CHROMATOGRAPHY

CLAIM OF PRIORITY

The present application claims priority from Japanese patent application JP 2015-041593 filed on Mar. 3, 2015, the content of which is hereby incorporated by reference into this application.

BACKGROUND

1. Technical Field

The present invention relates to a liquid analysis device.

2. Background Art

In liquid chromatography devices, ultraviolet (UV)/ultraviolet-visible (UV-VIS) absorbance detectors are most generally used. Particularly, the ultraviolet wavelength band (200 to 380 nm), in which the absorption wavelength bands of various functional groups in organic compounds are present, is being used in various fields. Advantages of the absorbance detector include sensitivity improvement by aligning the measurement wavelength with the wavelength of maximum absorption of substance, and the capability to measure a sample while suppressing the influence of an interfering object by using a measurement wavelength that decreases optical absorption of the interfering component. However, the UV detector cannot detect compounds that do not have absorption in the ultraviolet wavelength band, such as sugars and alcohols.

Research into far-ultraviolet spectroscopy has long been conducted, and it is known that even substances that have hardly any absorption in the ultraviolet region (200 nm or above) have an absorption band in the far-ultraviolet region without fail. However, research has been mostly focused on substances in gaseous phase state, and not much research into liquid state has been conducted. The reason is that, when a spectrum in the far-ultraviolet region is measured, it is necessary to evacuate the inside of the spectroscopic device because of strong absorption by oxygen in the air, making the device complex and expensive. In addition, the absorption spectrum of the solvent used has been so strong that hardly any light was transmitted, making the measurement difficult. Generally, far-ultraviolet light is defined as the light with wavelengths of 10 nm to 200 nm inclusive, while ultraviolet light (also called near-ultraviolet light) is defined as the light with wavelengths of 200 nm to 380 nm.

In recent years, it has become possible to perform far-ultraviolet spectrometry by substituting the air in the spectroscopic device with inert gas such as nitrogen gas. Accordingly, it is now possible to perform absorption spectrum measurement of substance in a solution up to 180 nm using a transmission-type cell with a shortened optical path length of 0.5 mm (Non-Patent Document 1). It is also possible to perform absorption spectrum measurement of liquids up to 120 nm using an attenuated total reflection (ATR) type of spectroscopic device with an extremely shortened effective optical path length of several tens of nm (Non-Patent Document 2).

As a device capable of measuring the reflectance and transmittance spectra of a solid sample in the far-ultraviolet region, a vacuum ultraviolet spectroscopic device is known. The device prevents a decrease in the intensity of incident light on a sample, and has achieved a decrease in measurement time as well as evacuation time by eliminating the need for sample inclination during reflectance measurement, thereby decreasing the size of a sample moving mechanism (Patent Document 1).

FIG. 10 is a schematic diagram of the conventional vacuum ultraviolet spectroscopic device. The light emitted from a light source 901 is passed through a slit 902 and enters a diffraction grating 904. The light of a predetermined wavelength passes through a slit 905, and the intensity of the light transmitted by a sample 909 is detected by a first photodetector 907. The spectroscopic device is provided with an evacuation mechanism 915 for eliminating the influence of optical absorption by oxygen or water vapor. In a typical spectroscope, the optical path is split by a beam splitter and the like installed immediately before the sample, creating reference light and light that is caused to enter the sample for absorbance detection, However, in Patent Document 1, a second photodetector 908 is moved in conjunction with rotation of the diffraction grating 904 using a drive device 910, and light of the same wavelength other than +1 order light is detected as the reference light by the second photodetector 908.

Nevertheless, the above-described devices all have as the primary objective the acquisition of an absorption spectrum, and have not been applied as a detector in liquid chromatography devices due to the issues of detection sensitivity, device size, cost and the like.

RELATED ART DOCUMENTS

[Patent Document]
  Patent Document 1: JP 2004-12370 A
[Non-Patent Documents]
  Non-Patent Document 1: Analytical Chemistry, 2005, Vol. 77, pp. 2272-2277.
  Non-Patent Document 2: REVIEW OF SCIENTIFIC INSTRUMENTS, Vol. 78, 103107.

SUMMARY

FIG. 11 is a diagram of a conventional absorbance detection device for liquid chromatography. In the conventional absorbance detection device for liquid chromatography, the light emitted from a light source 1001 that emits ultraviolet light or visible light is reflected by a mirror 1002, passes through an entrance slit 1003 and enters a diffraction grating 1004. Of the light dispersed by the diffraction grating 1004, light of a specific wavelength passes through an output slit 1005, is reflected by a mirror 1009, and then split by a beam splitter 1030 into two optical paths. One light enters a flow cell 1006, and the light transmitted by the flow cell 1006 is detected by a first photodetector 1007 as detection light. The other light is detected by a second photodetector 1008 as reference light. The optical intensities of the detection light and the reference light are transmitted to a computation unit 1020, which determines and outputs absorbance to a control unit 1021. Samples introduced from an auto-sampler 1014 are injected into an eluent 1010 delivered by a pump 1011, separated in a separating column 1012, successively introduced into the flow cell 1006, and sent to a waste fluid container 1013. By measuring a temporal change in absorbance at a specific wavelength with respect to each component separated by the separating column 1012, the concentration of each component can be determined.

In the far-ultraviolet region, in addition to the oxygen and water vapor in the atmosphere, the eluent (such as water or methanol) used for liquid chromatography also has very strong absorption, whereby the amount of light used for detection is decreased, making absorbance detection difficult. For example, in the case of water, an absorbance spectrum shown in FIG. 12 is known, where the absorbance is increased by a factor of four or more if the wavelength is changed from 200 nm to 180 nm. Generally, in a spectrophotometer, noise increases as the amount of light is decreased. The noise herein refers to the fluctuation absorbance in the absence of the sample to be measured. FIG. 13 is a diagram showing the relationship between the amount of light of an absorbance detector and noise. In the absorbance detector, the relationship is such that the noise value is inversely proportional to the amount of light. Accordingly, high sensitivity is difficult to achieve unless the amount of light can be ensured in the far-ultraviolet region.

In the conventional ATR type spectrophotometer, the optical path length is very small at several tens of nanometers, so that the absorbance of liquid such as water can be kept low and a sufficient amount of light can be ensured. However, because the optical path length is very small, sensitivity is greatly decreased. While absorption spectrum measurement for simple substance can be performed even when the sensitivity is low, the technology cannot be applied for liquid chromatography that requires high sensitivity. Because the components separated in the separating column will exist in the eluent only in minute amounts, the optical path length of the flow cell of a normal absorbance detection device for liquid chromatography is 10 mm.

Meanwhile, in the conventional vacuum spectroscopic device (FIG. 10), the amount of light in the far-ultraviolet region is ensured by adopting the optical system that does not use a. beam splitter. In this configuration, in order to acquire an absorbance spectrum, the second photodetector 908 operated in conjunction with the rotation of the diffraction grating 904 is used to detect, as the reference light, light of the same wavelength as the measurement wavelength and other than +1 order light. When the conventional vacuum spectroscopic device is applied in a liquid chromatographic detector, it is necessary to operate the second photodetector 908, measuring the reference light, in conjunction with the diffraction grating 904. Accordingly, the device becomes complex all the more for the drive device 910 for operating the second photodetector 908 in conjunction, resulting in an increase in cost. Furthermore, the volume of the device is increased by the installation, of the drive device 910, causing problems such as a decrease in efficiency of evacuation or purging by inert gas such as nitrogen gas, or a time increase.

A far-ultraviolet absorbance detection device for liquid chromatography according to the present invention includes: an optical system including a light source that emits light including far-ultraviolet light, a diffraction grating that disperses the light emitted from the light source, a flow cell through which a liquid is passed, a slit for selecting a predetermined wavelength of +1 order light diffracted by the diffraction grating and causing the light to enter the flow cell, a first photodetector that detects the light transmitted by the flow cell, and a second photodetector that detects light other than the +1 order light diffracted by the diffraction grating; a mechanism for evacuating or substituting the optical system with nitrogen gas; and a computation unit that calculates absorbance from an output signal from the first photodetector and an output signal from the second photodetector. The second photodetector is fixedly disposed.

According to an example, the second photodetector may be fixedly disposed on a −1 order light side of the diffraction grating, and the wavelength width of the light detected by the second photodetector may be set to be greater than the wavelength width of the light detected by the first photodetector.

Preferably, the computation unit may perform base line correction in synchronism with wavelength modification during measurement.

According to an example, the wavelength width of the light detected by the second photodetector may be 4 nm to 50 nm inclusive.

According to the present invention, absorbance measurement can be performed with a sufficient amount of light and without causing a decrease in the amount of detection light. Further, the need for a drive device for driving a reference light photodetector in conjunction with a diffraction grating can be eliminated, and the number of components of the optical system can be decreased, whereby the efficiency of evacuation or purging by inert gas such as nitrogen gas can be increased while achieving a decrease in the time required.

Other problems, features, and effects will become apparent from the following description of an embodiment.

DETAILED DESCRIPTION OF THE EMBODIMENT

In the following, an embodiment of the present invention will be described with reference to the drawings.
[Embodiment]

In the present embodiment, an example will be described in which a photodetector for measuring reference light is fixedly disposed on the −1 order light side of a diffraction grating so as to measure absorbance.

Figure 1:
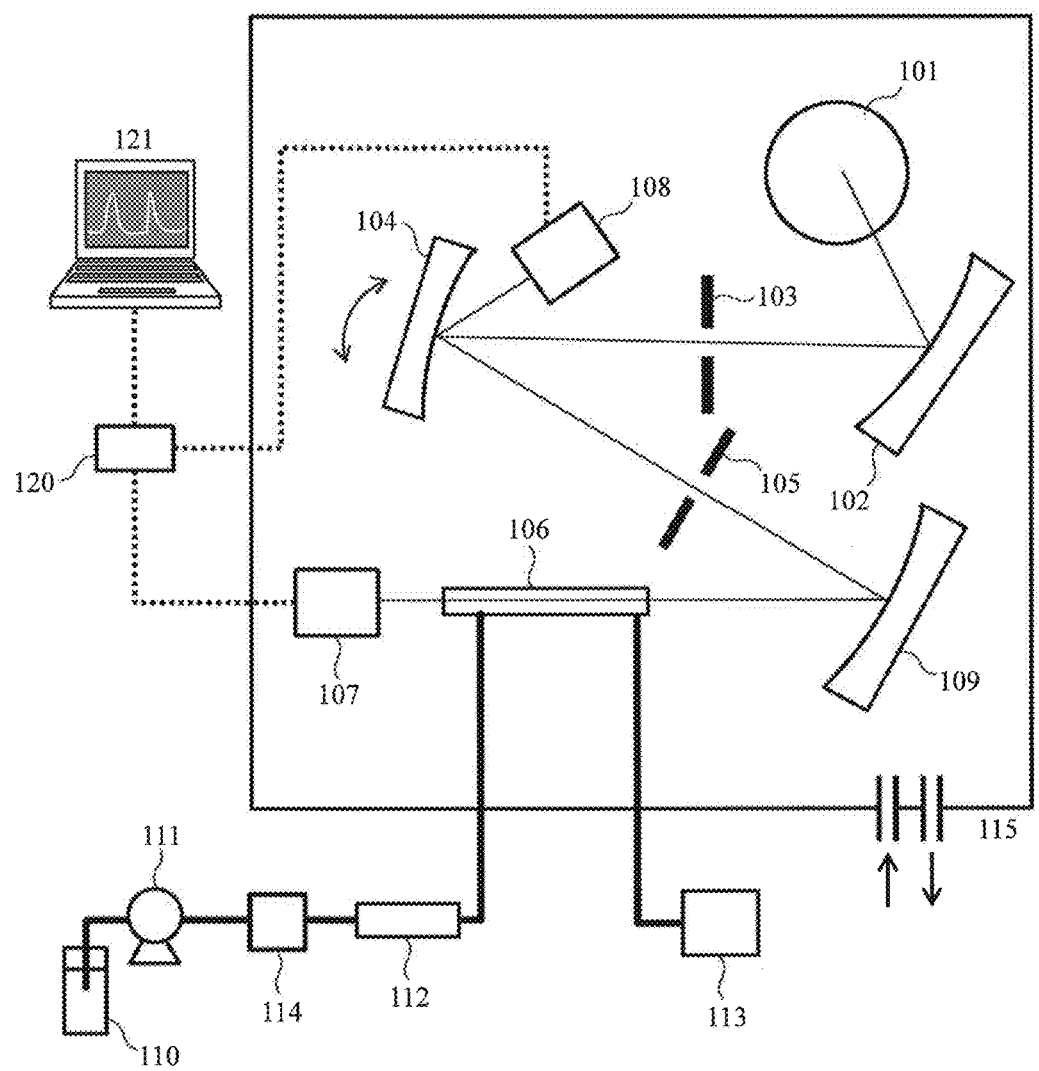
FIG. 1 is a schematic view of an embodiment of a far-ultraviolet absorbance detection device for liquid chromatography according to the present invention.

FIG. 1 is a schematic view illustrating an embodiment of a far-ultraviolet absorbance detection device for liquid chromatography according to the present invention. The far-ultraviolet absorbance detection device for liquid chromatography according to the present embodiment includes a deuterium lamp 101, a first mirror 102, an entrance slit 103, a concave diffraction grating 104 as a spectroscopic element, an output slit 105, a second mirror 109, a flow cell 106, a detection light photodetector 107, a reference light photodetector 108, and a sealed container 115. The detection device is connected to a container of eluent 110, an auto-sampler 114, a pump 111, a separating column 112, and a waste fluid container 113.

The light emitted from the deuterium lamp 101 is reflected by the first mirror 102, condensed at an opening portion of the entrance slit 103, and enters the concave diffraction grating 104. The light of a specific wavelength of +1 order light dispersed by the concave diffraction grating 104 passes through the output slit 105, and the light reflected by the second mirror 109 is guided to the flow cell 106. The light transmitted by the flow cell 106 is detected by the detection light photodetector 107. The entrance slit 103 and the output slit 105 are installed on the Rowland circle of the concave diffraction grating 104. On the other hand, the −1 order light dispersed by the concave diffraction grating 104 is detected by the reference light photodetector 108 fixedly disposed in the device.

Samples introduced from the auto-sampler 114 are injected into the eluent 110 delivered by the pump 111, separated by the separating column 112, successively introduced into the flow cell 106, and sent to the waste fluid container 113. Depending on the type of the sample liquid separated by the separating column 112 or a change in the concentration thereof, the amount of light transmitted by the flow cell 106 varies. The amount of light detected by the detection light photodetector 107 and the amount of light detected by the reference light photodetector 108 are processed by the computation unit 120 and output to the control unit 121 as an absorbance.

Because far-ultraviolet light is absorbed by oxygen and water vapor, the optical system as a whole is hermetically sealed in the sealed container 115, and the inside of the sealed container 115 is substituted with nitrogen gas or evacuated, so as to prevent a decrease in the amount of light in the optical path. For example, by implementing nitrogen purge, the amount of detection light of wavelength 185 nm is approximately doubled. Desirably, the evacuation or nitrogen purge is implemented prior to turning on the deuterium lamp 101. This is because if far-ultraviolet light of short wavelengths is emitted in the atmosphere containing oxygen, a window material of synthetic silica and the like may become fogged, causing a decrease in the amount of light.

While in the present embodiment the deuterium lamp 101 is used as the light source, a light source that emits a wide wavelength band of light including far-ultraviolet light and ultraviolet light may preferably be used, such as a mercury lamp or an excimer lamp. In the present invention, the far-ultraviolet light that can be used in the liquid chromatographic absorption detector is defined as light of wavelengths of 170 nm to 200 nm inclusive, which is not readily subject to the influence of absorption by water (peak wavelength around 150 nm).

The mirrors 102 and 109 are preferably coated with material that has small reflection loss with respect to far-ultraviolet light and ultraviolet light. Preferable examples of the coating material include aluminum and $MgF_2$. For the two photodetectors 107 and 108, photodiodes having a wide linearity range are preferable for the liquid chromatography purpose. However, a photomultiplier or a photodiode array and the like may be used. The window material used for the deuterium lamp 101, the flow cell 106, and the photodetectors 107 and 108 preferably has high transmittance for far-ultraviolet light and ultraviolet light. Preferable examples include synthetic silica, $MgF_2$, and $CaF_2$.

When the absorbance of a sample at a predetermined wavelength is determined in a normal vacuum ultraviolet spectrophotometer, it is necessary to make the wavelength of the reference light identical to that of the detection light. Meanwhile, in a liquid chromatograph, a temporal change in the absorbance at a predetermined wavelength is measured so as to measure the type or concentration of the sample. In a narrow wavelength range (such as not longer than 50 nm), the wavelength dependency of the light source fluctuation is small, so that even when the reference light does not have the same wavelength as that of the detection light, there will be no increase in noise compared with when the same wavelength is used. Accordingly, the light of a different wavelength from the detection light may be used as the reference light. Thus, in the present embodiment, the reference light photodetector 108 is fixedly disposed at a position enabling the measurement of −1 order light dispersed by the concave diffraction grating 104.

Figure 11:
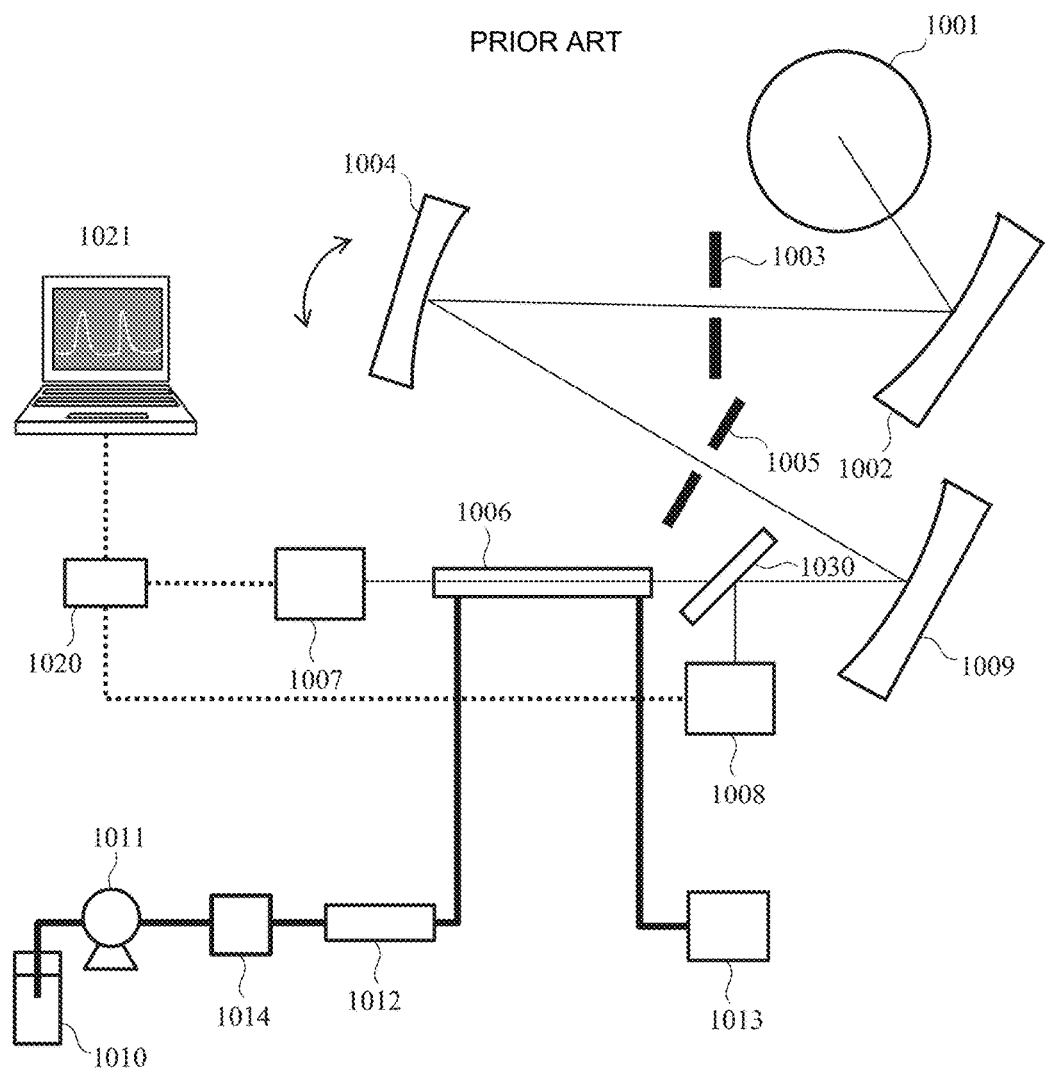
FIG. 11 is a diagram for describing a conventional absorbance detection device for liquid chromatography.
Figure 12:
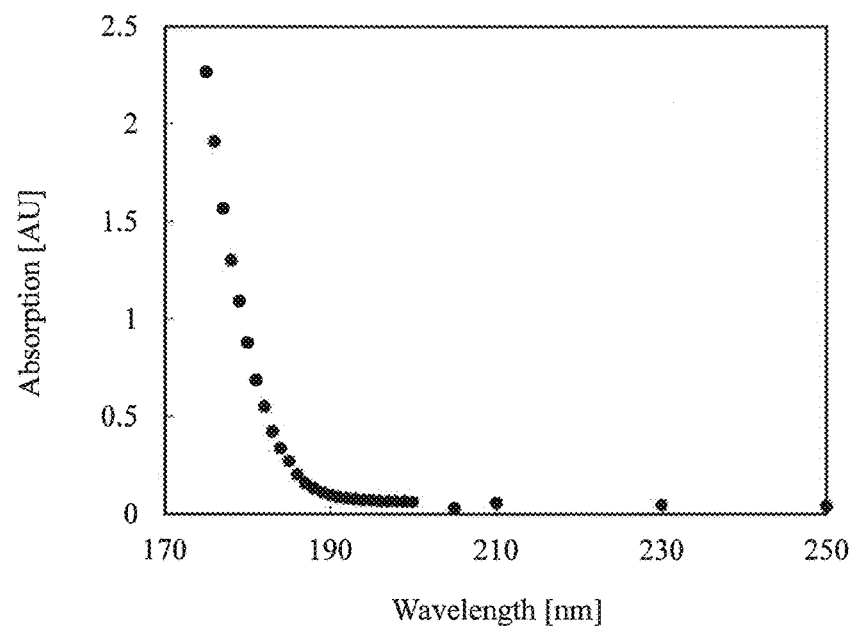
FIG. 12 illustrates an absorption spectrum of water.
Figure 13:
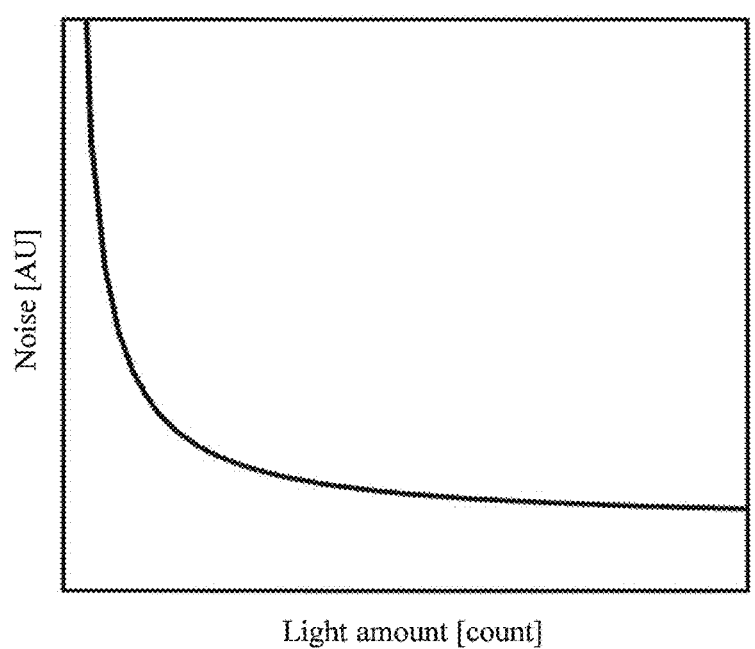
FIG. 13 illustrates the relationship between the amount of light of an absorbance detector and noise.

By adopting the optical system of the present embodiment, the amount of detection light is increased compared with when the beam splitter 1030 of the conventional spectrophotometer is used (FIG. 11). For example, compared with when a half mirror is used as the beam splitter 1030, the amount of detection light is doubled in the optical system of the present embodiment. The wavelength of the reference light need not be limited to a single wavelength, and the light of a predetermined wavelength band including a plurality of wavelengths may be utilized. Namely, the wavelength width of the light detected by the reference light photodetector 108 may be set to be greater than the wavelength width of the light detected by the detection light photodetector 107. For example, when the light of a wavelength band with a wavelength width of 4 nm to 50 nm inclusive including part or all of the far-ultraviolet region (170 nm to 200 nm) is utilized as the reference light, the amount of reference light will not be readily changed greatly even when the measurement wavelength is modified, providing the advantage that the absorbance measurement is stabilized. When the wavelength width of the reference light is on the same order as the wavelength width of the detection light (the wavelength width of the detection light is not greater than 4 nm), the light utilized as reference light is the light that is other than the +1 order light of the concave diffraction grating 104 and that is different from the detection wavelength. However, when the wavelength width of the reference light is 4 nm or longer, light other than +1 order light and of the same wavelength as that of the detection light may be included. The light used as reference light is not limited to the −1 order light of the concave diffraction grating 104 and may include light of ±2 order or above, or 0 order light. Further, the position at which the reference light photodetector 108 is disposed may not be on the Rowland circle.

Figure 2:
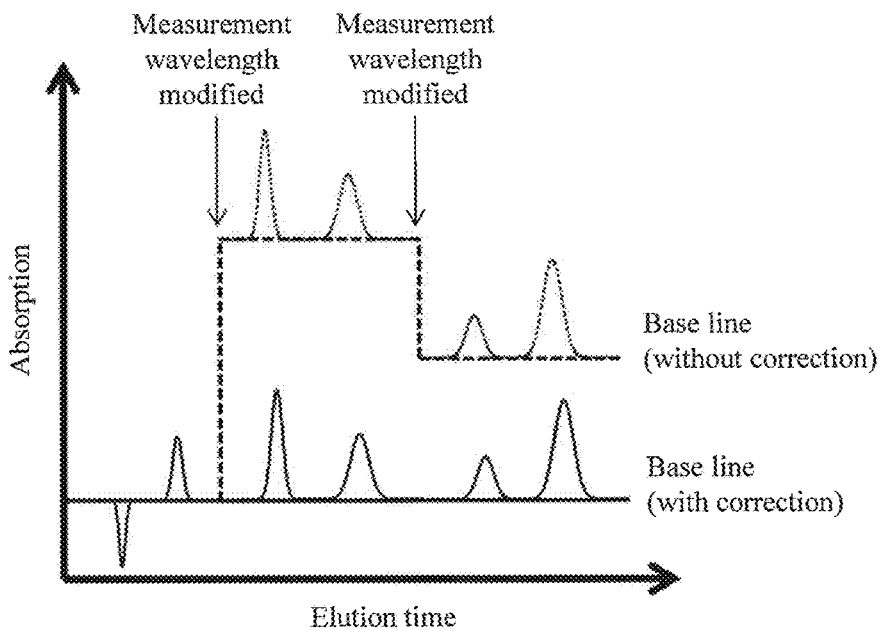
FIG. 2 is a diagram for describing a base line variation as a result of measurement wavelength modification.

FIG. 2 is a diagram for describing a base line variation as a result of measurement wavelength modification. Because the reference light photodetector 108 is fixedly disposed, modification of the measurement wavelength by the user causes rotation of the concave diffraction grating 104 and leads also to a modification of the wavelength of the reference light. Accordingly, if the wavelength is modified during measurement, the base line varies as schematically illustrated in FIG. 2, making quantitative absorbance measurement impossible. Thus, in the present embodiment, the base line for absorbance is corrected in synchronism with the wavelength setting during measurement.

Figure 3:
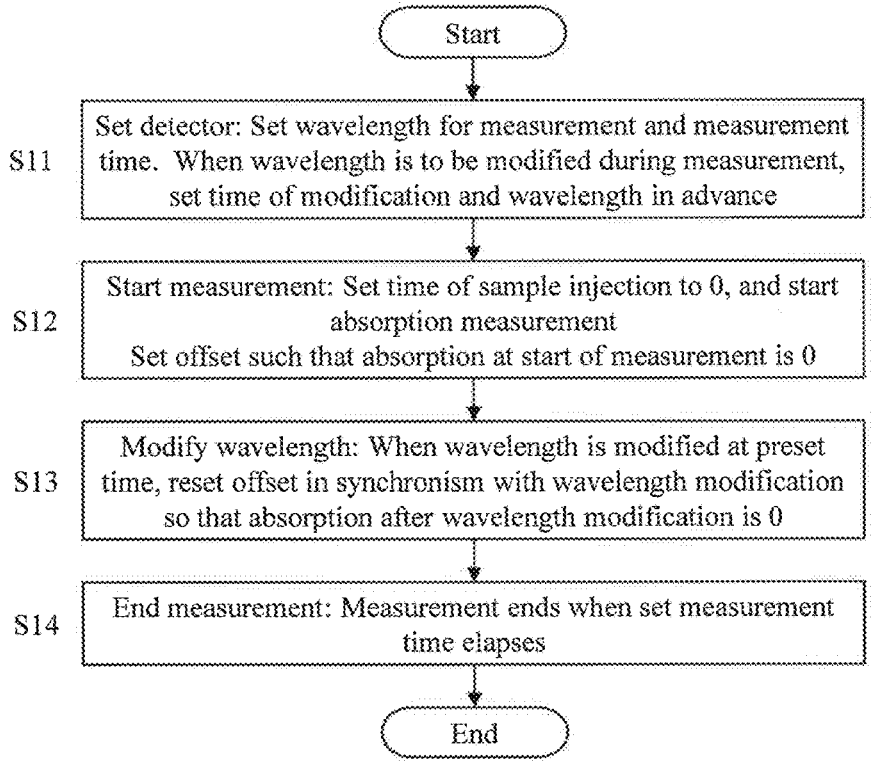
FIG. 3 is a flowchart of a base line correction procedure at the time of measurement wavelength modification.

FIG. 3 is a flowchart illustrating a procedure for base line correction at the time of measurement wavelength modification.

Prior to the start of measurement, the measurement wavelength and the measurement time are set. If the wavelength is to be modified during measurement, the time for modification and the wavelength after modification are set in advance (S11). The time for modifying the measurement wavelength is assumed to be the time at which the sample is not eluted and only the eluent is eluted. Then, the time at which the absorbance measurement is started and the sample is injected is set to be 0 second, and an offset is set so that the absorbance becomes zero at the start of measurement (0 second) (S12). After a certain time has elapsed and the wavelength modification time set in S11 is reached, the base line is corrected in synchronism with the wavelength modification, and the offset is again set so that the absorbance becomes zero (S13). When the wavelength is modified a plurality of times, step S13 is repeated. When the set measurement time has elapsed, the measurement is completed (S14).

"In synchronism with the wavelength modification" refers to the same time as the time of wavelength modification, or within a certain time (hereafter referred to as the correction time) from the time of modification. The correction time is the time it takes for the absorbance to become stabilized, and is determined from the sampling interval or integrated time of measurement. By making the correction time not more than 10 times the sampling interval or not more than three times the integrated time, the corrected absorbance value can be stabilized. A preferable correction time is normally within 1 to 2 seconds, The base line correction is performed by recording the absorbance at a certain predetermined time within the correction time or an average value of absorbance within a certain time, and then setting the offset so as to make the absorbance zero.

Figure 4:
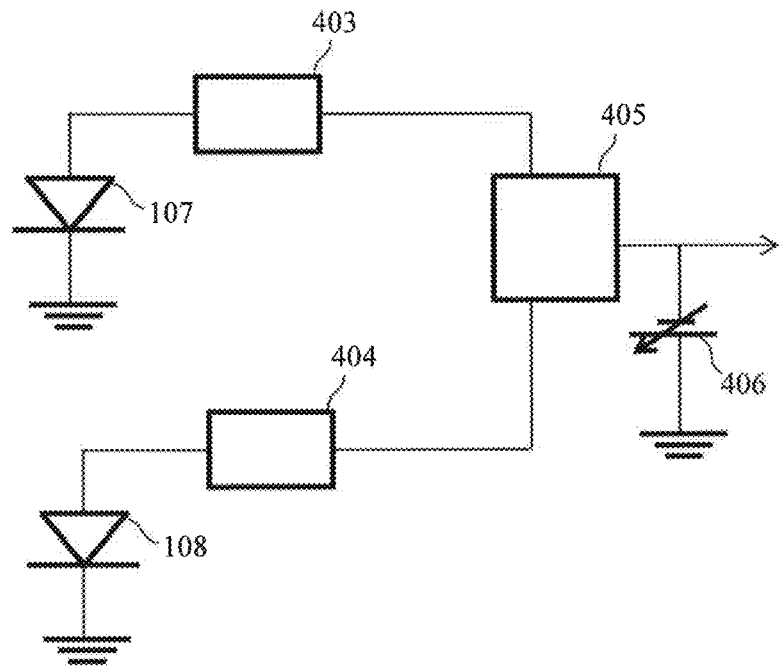
FIG. 4 is a schematic view of a part of a computation unit.

FIG. 4 is a schematic view illustrating a part of the computation unit 120. Signals corresponding to the amounts of light detected by the detection light photodetector 107 and the reference light photodetector 108 are respectively converted into voltages and amplified by signal processing circuits 403 and 404, and converted into an absorbance signal by an absorbance computation circuit 405. A voltage value for a variable voltage source 406 for correction is set in accordance with the absorbance detected in synchronism with the wavelength modification, and a voltage value that cancels the absorbance is output so as to correct the base line. The base line correction may be performed by software in the control unit 121.

Figure 5:
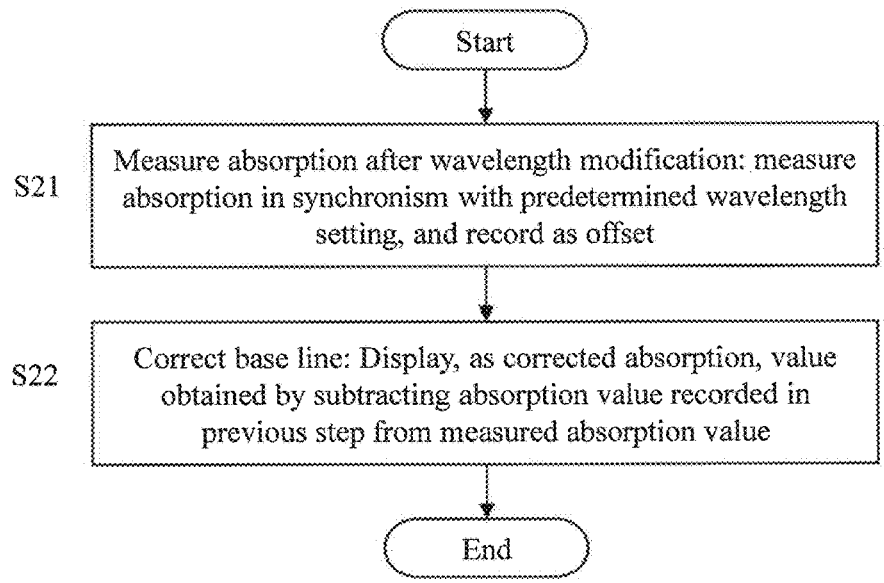
FIG. 5 is a flowchart of a base line correction, process procedure by software.

FIG. 5 is a flowchart illustrating the procedure for a base line correction process by software. In synchronism with the setting of the wavelength modification, the absorbance signal output from the computation unit 120 is recorded as an offset (S21), and the base line is corrected by subtracting the recorded offset signal from a subsequently obtained absorbance signal (S22). When the wavelength is modified a plurality of times, the base line is corrected each time the wavelength is modified.

[First Measurement Example]

An example of sugar analysis using the far-ultraviolet absorbance detection device for liquid chromatography according to the embodiment will be described. In this measurement, the reference light photodetector was fixedly disposed at a position spaced apart from the Rowland circle on the −1 order light side toward the outside by 5 mm. The position was such that when the wavelength of the detection light was 185 nm, the reference light of a wavelength band of 170 to 200 nm entered the reference light photodetector. The analysis conditions used are indicated below.

Figure 6:
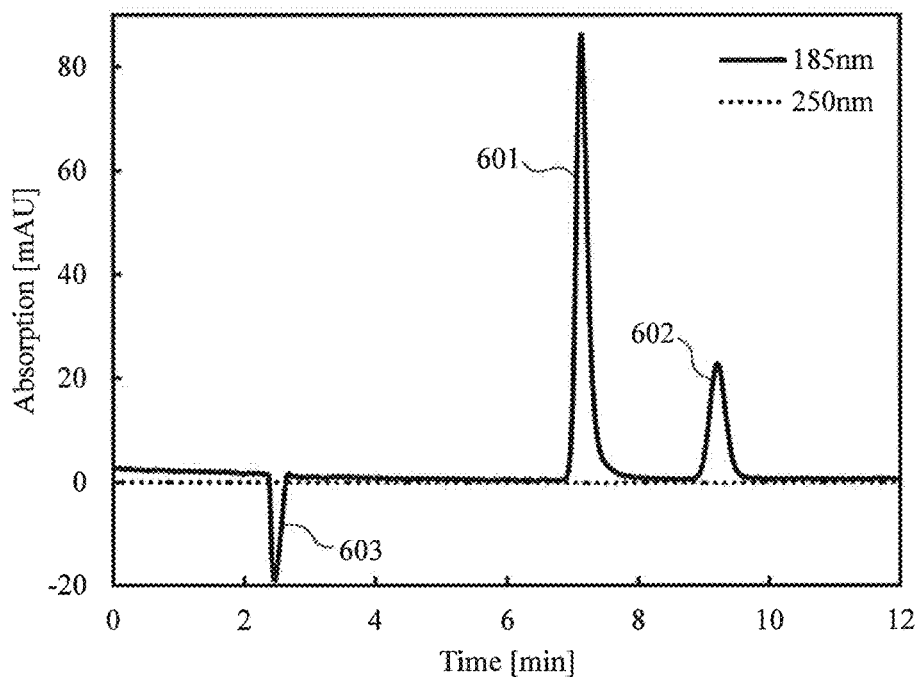
FIG. 6 illustrates an example of sugar analysis.
Figure 7:
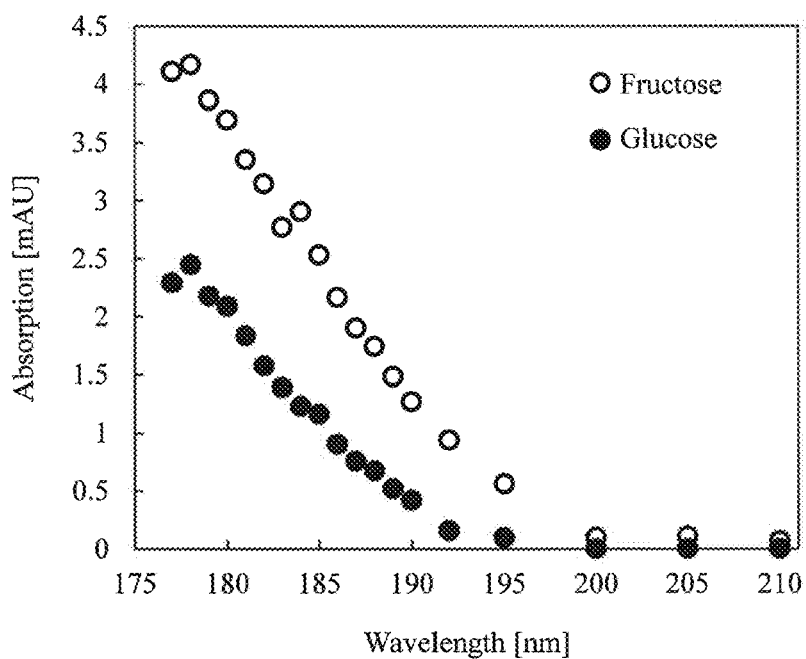
FIG. 7 illustrates an example of measurement of absorption spectrum of sugar.

Sample: Mixed aqueous solution of fructose and glucose each of concentration of 5 mg/mL
Injected amount: 6 μL
Analysis column: A column manufactured by SHODEX (Asahipak NH2P-50 4E, 4.6 mm×250 mm)
Mobile phase: Mixed solution of 25% water and 75% acetonitrile
Flow rate: 1.0 mL/min
Detection wavelength: 185 nm FIG. 6 illustrates an example of sugar analysis by measurement using the present device, where a flow cell with an optical path length of 10 mm was used. As indicated by a broken line in FIG. 6, detection of sugar was difficult with the wavelength 250 nm of ultraviolet light. On the other hand, as indicated by a solid line in FIG. 6, by using the wavelength 185 nm of far-ultraviolet light, absorbance peaks of fructose 601 and glucose 602 were separated and detected following a solvent peak 603. For mobile phase, it is preferable to use water or acetonitrile that has hardly any absorption at the wavelengths of 170 to 200 nm of the far-ultraviolet region, or a mixture thereof FIG. 7 illustrates an example of measurement of sugar absorption spectra using a flow cell with the optical path length of 0.5 mm under the same measurement conditions. The spectra of FIG. 7 indicate that measurement by ultraviolet light was difficult due to low sensitivity, and that sugar measurement was enabled by the use of far-ultraviolet light.

By using the light of a different wavelength from the detection light as the reference light in the device configuration of the embodiment, the amount of +1 order light as the detection light increased by five times or more, and spectrum measurement up to 175 nm became possible, compared with an optical system using a conventional beam splitter where there was hardly any amount of light. Because as the reference light, light of a wider wavelength band than the detection light (the wavelength band of 170 to 200 nm for the reference light against the detection wavelength of 185 nm) is used, there is the advantage that the amount of reference light is not greatly changed even when the measurement wavelength is modified. Further, the wavelength dependency of the light source fluctuation is so small as to be negligible when the wavelength range is narrow (wavelength width 30 nm) as in the present case, and the noise caused by the light source fluctuation was decreased by the present system.

[Second Measurement Example]

An example of peptide analysis using the far-ultraviolet absorbance detection device for liquid chromatography according to the embodiment will be described. The analysis conditions used are as follows.

Figure 8:
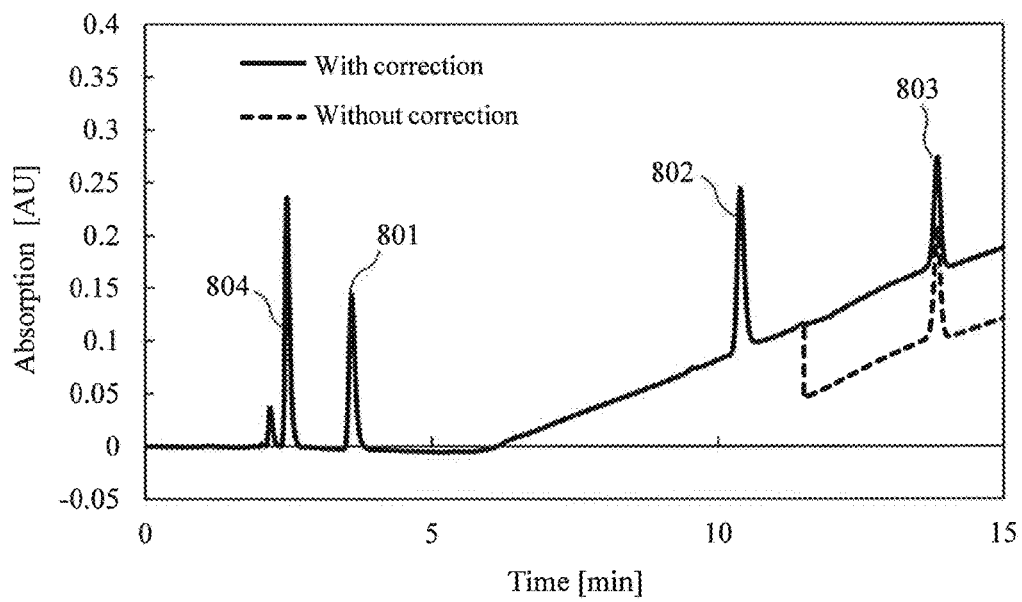
FIG. 8 illustrates an example of peptide analysis.
Figure 9:
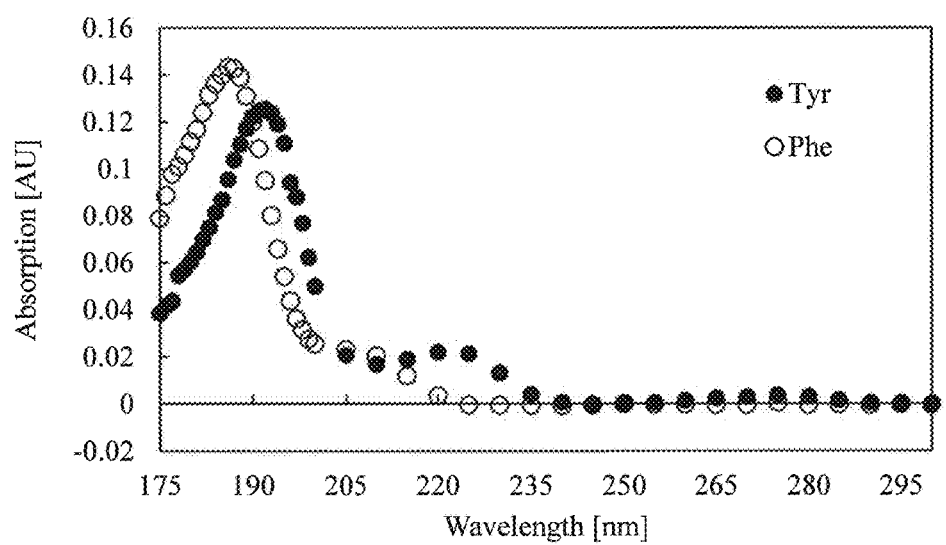
FIG. 9 illustrates absorption spectra of Tyr and Phe.
Figure 10:
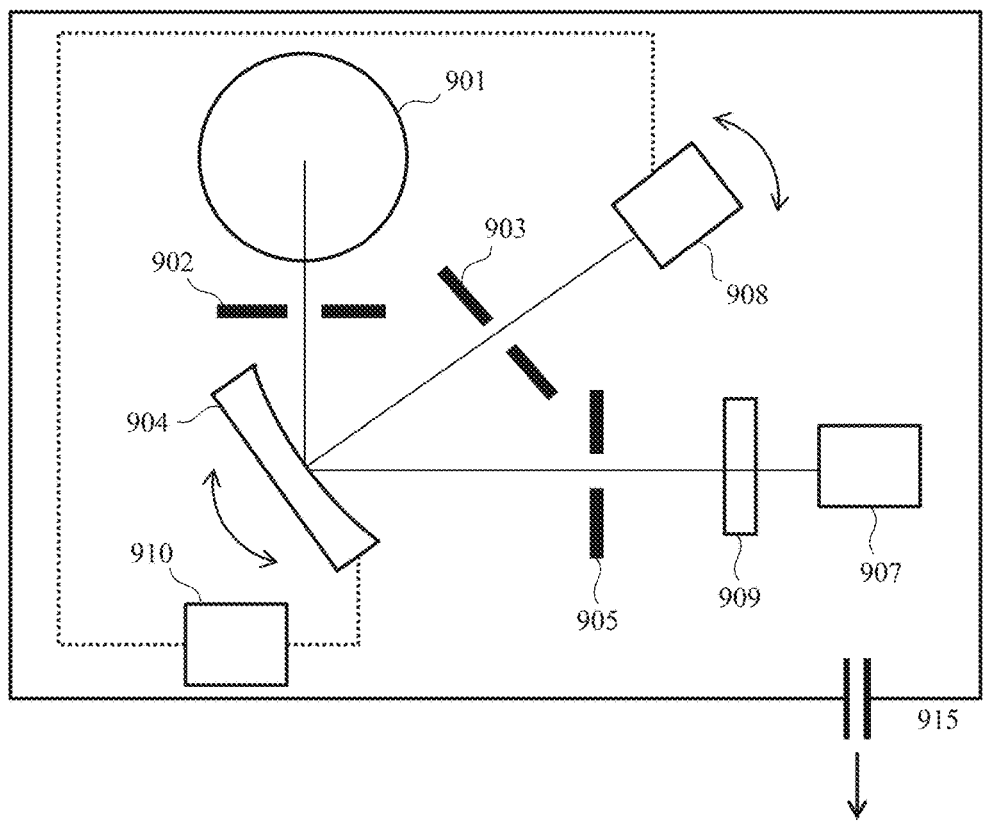
FIG. 10 is a schematic diagram of a conventional vacuum ultraviolet spectroscopic device.

Sample: Gly-Tyr, Val-Tyr-Val, and Phe-Asp-Phe-Ser-Phe each with concentration of 0.01 mg/mL
Injected amount: 10 μL,
Analysis column: A column manufactured by Vydac (218TP54, 4.6 mm×250 mm)
Mobile phase: Gradient analysis in which the composition was linearly changed from a mixed solution with 90% water and 10% acetonitrile to a mixed solution with 60% water and 40% acetonitrile over a period of 30 minutes. 5 mM of sodium perchlorate salt was added.
Flow rate: 1.0 mL/min FIG. 8 illustrates an example of peptide analysis by measurement using the present device. FIG. 9 illustrates the absorption spectra of Tyr and Phe. In this measurement, the wavelength at the start of measurement (0 mm) set to 192 nm, and the measurement wavelength after the elapse of 11.5 min was set to 187 nm. This is because, as illustrated in FIG. 9, while the absorption peak wavelength of Tyr in the far-ultraviolet region is at 192 nm, the absorption peak wavelength of Phe in the far-ultraviolet region is at 187 nm.

By modifying the wavelength from 192 nm to 187 nm, the sensitivity of detection of peptide including Phe can be increased approximately by a factor of 1.5.

The reference light photodetector was fixedly disposed at a position away from the Rowland circle on the −1 order light side by 5 mm toward the outside, as in the first measurement example. When the wavelength of the detection light was 192 nm, the reference light of a wavelength band of 170 to 200 nm was caused to enter the reference light photodetector. When the wavelength of the detection light was 187 nm, the reference light of a wavelength band of 176 to 206 nm was caused to enter the reference light photodetector.

For peptide separation, sodium perchlorate having hardly any absorption in the far-ultraviolet region was used as an ion pair reagent. Another example of salt having no absorption in the far-ultraviolet region is sodium fluoride. Following a solvent peak 804, Gly-Tyr 801, Val-Tyr-Val 802, and Phe-Asp-Phe-Ser-Phe 803 were separated, and their respective absorption peaks were able to be measured at high sensitivity using far-ultraviolet light. Correction of the base line for the wavelength change after 11.5 min was implemented by software after the measurement. By the base line correction, quantitativity can be further increased, When the elution time is known as in the present measurement example, detection can be performed. with even higher sensitivity by setting the absorption peak wavelength for each component at the measurement wavelength, By using, as the reference light, light of a different wavelength from the detection light according to the device configuration of the embodiment, the amount of +1 order light as the detection light increased by a factor of 2 compared with the amount of light obtained by the optical system using a conventional beam splitter, and the absorbance noise decreased approximately by a factor of 2 and stood at 10 µAU, making high-sensitivity peptide measurement possible. Because as the reference light the light of a wavelength band wider than the detection light is used, there is the advantage that the amount of reference light is not greatly changed even when the measurement wavelength is modified. Further, the wavelength dependency of the light source fluctuation is so small as to be almost negligible when the wavelength range is narrow (wavelength width 30 nm) as in the present case. Accordingly, the noise caused by light source fluctuation can be decreased by the present system, and high sensitivity measurement can be performed.

The present invention is not limited to the above-described embodiment and may include various modifications. The embodiment has been described in detail for aiding in understanding the present invention, and the invention is not limited to the embodiment having all of the described features. Part of the configuration of one embodiment may be replaced with the configuration of another embodiment, or the configuration of the other embodiment may be incorporated into the configuration of the one embodiment. With respect to part of the configuration of each embodiment, addition of another configuration, deletion, or substitution may be made.

DESCRIPTION OF SYMBOLS

101 Deuterium lamp
104 Concave diffraction grating
106 Flow cell
107 Detection light photodetector
108 Reference light photodetector
110 Fluent
111 Pump
112 Separating column
113 Waste fluid container
114 Auto-sampler
115 Sealed container
120 Computation unit
121 Control unit
910 Drive device
1030 Beam splitter

What is claimed is:

1. A far-ultraviolet absorbance detection device for liquid chromatography, comprising:
   an optical system including a light source that emits light including far-ultraviolet light,
   a first mirror disposed adjacent to the light source,
   a first slit disposed adjacent to the first mirror,
   a diffraction grating that disperses the light emitted from the light source, the diffraction grating being adjacent to the first slit and configured to rotate,
   a flow cell through which a liquid is passed,
   a second slit for selecting a predetermined wavelength of +1 order light diffracted by the diffraction grating and causing the light to enter the flow cell,
   a second mirror disposed adjacent to the second slit,
   a first photodetector that detects the light transmitted by the flow cell,
   a second photodetector that detects light other than the +1 order light diffracted by the diffraction grating;
   a mechanism for evacuating or substituting the optical system with nitrogen gas; and
   a computation unit that calculates absorbance from an output signal from the first photodetector and an output signal from the second photodetector, wherein
      the second photodetector is fixedly disposed relative to the diffraction grating and is adjacent to the diffraction grating, such that no structure is interposed between the second photodetector and the diffraction grating,
      light from the diffraction gradient passes directly into the second photodetector without passing through any slit and without passing through any beam splitter,
      light reflected from the second mirror passes directly into the flow cell without passing through any slit and without passing through any beam splitter, and
      the computation unit performs base line correction in synchronism with wavelength modification caused by rotation of the diffraction grating during measurement.

2. The far-ultraviolet absorbance detection device for liquid chromatography according to claim 1, wherein
   the first mirror is disposed adjacent to the light source, with nothing interposed therebetween,
   the first slit is disposed adjacent to the first mirror, with nothing interposed therebetween,
   the diffraction grating is adjacent to the first slit, with nothing interposed therebetween,
   the second mirror is disposed adjacent to the second slit, with nothing interposed therebetween, and
   the second photodetector is adjacent to the diffraction grating, with nothing interposed therebetween.

3. The far-ultraviolet absorbance detection device for liquid chromatography according to claim 2, wherein the second photodetector is fixedly disposed on a −1 order light side of the diffraction grating, and a wavelength width of the light detected by the second photodetector is greater than a wavelength width of the light detected by the first photodetector.

4. The far-ultraviolet absorbance detection device for liquid chromatography according to claim 2, wherein a wavelength width of the light detected by the second photodetector is 4 nm to 50 nm inclusive.

5. The far-ultraviolet absorbance detection device for liquid chromatography according to claim 2, wherein the light source is turned on after the optical system is substituted with nitrogen gas.

6. The far-ultraviolet absorbance detection device for liquid chromatography according to claim 2, wherein the liquid passed through the flow cell is water or acetonitrile, or a mixture thereof.

7. The far-ultraviolet absorbance detection device for liquid chromatography according to claim 6, wherein the liquid includes a salt which is sodium perchlorate or sodium fluoride.

* * * * *